United States Patent [19]

Graether

[11] Patent Number: 5,322,054
[45] Date of Patent: Jun. 21, 1994

[54] PUPIL EXPANDER CARRIER AND MEANS FOR MANIPULATING A PUPIL EXPANDER

[76] Inventor: John M. Graether, 611 Elmwood Dr., Marshalltown, Iowa 50158

[21] Appl. No.: 959,055

[22] Filed: Oct. 9, 1992

Related U.S. Application Data

[63] Continuation-in-part of Ser. No. 836,361, Feb. 18, 1992, Pat. No. 5,267,553.

[51] Int. Cl.$^5$ .................... A61B 17/02; B23Q 3/00
[52] U.S. Cl. ...................... 128/20; 606/107; 269/303
[58] Field of Search ............... 128/20, 3; 606/107, 606/166; 623/4; 269/303, 305

[56] References Cited

U.S. PATENT DOCUMENTS

| | | | |
|---|---|---|---|
| 1,105,641 | 8/1914 | Feaster | 269/305 X |
| 2,147,800 | 1/1937 | Sadowski | 269/305 |
| 2,464,114 | 3/1949 | Bloecher | 269/303 X |
| 2,812,758 | 11/1957 | Blumenschein | 128/20 |
| 3,807,393 | 4/1974 | McDonald | 128/20 |
| 4,387,706 | 6/1983 | Glass | 128/20 |
| 4,452,235 | 6/1984 | Reynolds | 623/5 |
| 4,684,113 | 8/1987 | Douglas et al. | 269/303 C |
| 4,906,247 | 3/1990 | Fritch | 606/107 X |
| 4,911,158 | 3/1990 | Weatherly | 606/107 |

*Primary Examiner*—Richard J. Apley
*Assistant Examiner*—Donna L. Maraglio
*Attorney, Agent, or Firm*—Zarley, McKee, Thomte, Voorhees & Sease

[57] ABSTRACT

A pupil expander carrier has a block having a support surface. A first post extends upwardly from this surface in spaced relation to a first pair of spaced secondary posts. These three posts normally hold and stabilize a circular pupil expander during storage conditions. A second pair of spaced secondary posts extend upwardly from the support surface and are spaced from said first post a distance greater than the normal diameter of the pupil expander whereby when the pupil expander is moved to supporting engagement with the first post and the second pair of secondary posts, it is changed from a circular configuration to an elongated and generally rectangular configuration. A retention post extends outwardly from an edge portion of the block adjacent the second pair of secondary posts to engage the strap of the pupil expander just before removal thereof from the block. The forceps used to remove the elongated pupil expander from the carrier block have two elongated forcep tips which are rectangular in cross section and which have a width greater than the height thereof for insertion in the outer peripheral opening of the pupil expander.

7 Claims, 2 Drawing Sheets ium, Dow Corning, durometer value of about 80) with
PUPIL EXPANDER CARRIER AND MEANS FOR MANIPULATING A PUPIL EXPANDER This application is a continuation-in-part of Ser. No. 07/836,361, filed Feb. 18, 1992, now U.S. Pat. No. 5,267,553.

BACKGROUND OF THE INVENTION

The pupil expander of my application Ser. No. 07/836,361, comprises a ring of silicone or other suitable soft plastic tubular material (e.g. Silastic ® silicone, Dow Corning, durometer value of about 80) with an outside diameter of 8.2 millimeters and an inside diameter of 7.0 millimeters. The ring has a "C" cross section configuration with a peripheral opening at the outside edge. The ring is incomplete with approximately a 3.5 millimeter gap to permit surgical maneuvers within it, and that gap is bridged by a strap between the open ends of the ring. There are also two tabs with holes, which are used for manipulation of the device inside and outside the eye.

The method of use of this pupil expander comprises the moving of the pupil expander, which is inserted into the anterior chamber of the eye through a previously prepared scleral incision. The expander is advanced across the anterior chamber until the flared end of the expander engages the iris at a 6 o'clock position. A spatula or lens manipulator is used to hold the expander in place against the iris sphincter while the forceps tips are partially withdrawn. The tips are then closed on the expander, and the tips are advanced into the eye causing the expander to enlarge horizontally engaging additional iris. The tips are then withdrawn an additional millimeter or two, and the above maneuver is repeated until the expander has been advanced onto the sphincter and the pupil has been gradually dilated. When the forceps have been withdrawn until they are opposite the tabs on the expander, the handle is lifted pushing the tips and the contained expander down toward the lens permitting the tabs to come down against the iris and completing the placement of the expander entirely within the pupil.

When the surgical maneuvers are completed, a small scissors is used to cut the silicone strap joining the ends of the pupil expander, and a forceps is used to lift one end of the expander by grasping the tab and moving it toward the center and lifting it to disengage the iris. Once one edge has been disengaged from the sphincter, the expander can simply be pulled from the eye under a layer of viscoelastic material.

Because of the extremely small size of the pupil expander, the handling thereof is very delicate and sensitive, and ordinary forceps are not adapted for easily handling thereof. In addition, the strap of the ring sometimes gets in the way of grasping the pupil expander for removal thereof from a carrier device.

It is therefore a principal object of the invention to provide means for easily grasping and manipulating the pupil expander of my co-pending application.

A further object of the invention is to provide a carrier means for storage of the pupil expander which facilitates the elongation and ultimate removal of the pupil expander therefrom at the time of use thereof.

These and other objects will be apparent to those skilled in the art.

SUMMARY OF THE INVENTION

The pupil expander carrier of this invention is comprised of a block having a support surface. A first post extends upwardly from this surface in spaced relation to a first pair of spaced secondary posts. These three posts normally hold and stabilize a circular pupil expander during storage conditions.

A second pair of spaced secondary posts extend upwardly from the support surface and are spaced from said first post a distance greater than the normal diameter of the pupil expander whereby when the pupil expander is moved to supporting engagement with the first post and the second pair of secondary posts, it is changed from a circular configuration to an elongated and generally rectangular configuration. A retention post extends outwardly from an edge portion of the block adjacent the second pair of secondary posts to engage the strap of the pupil expander just before removal thereof from the block.

The forceps used to remove the elongated pupil expander from the carrier block have two elongated forcep tips which are rectangular in cross section and which have a width greater than the height thereof for insertion in the outer peripheral opening of the pupil expander.

DESCRIPTION OF THE PREFERRED EMBODIMENT

Figure 8:
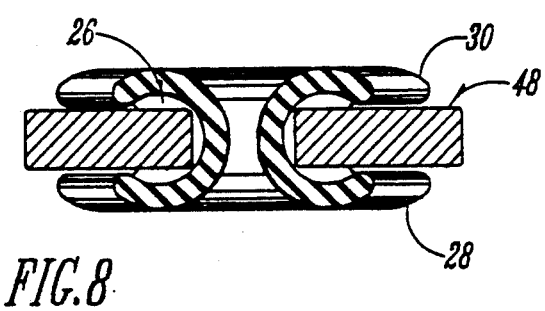
FIG. 8 is an enlarged scale sectional view taken on line 8—8 of FIG. 7.

The pupil expander 10 (FIG. 1) is comprised of a hollow ring member 12 which has opposite ends 14 and 16. Tabs 18 and 20 are formed adjacent the ends 14 and 16, respectively, and each tab has an aperture 22 therein. A strap 24 extends between tabs 18 and 20 to hold the ring member 12 in its circular configuration. It should be noted that the pupil expander 10 is of one-piece integral construction. The ring member is normally in the circular configuration shown in FIGS. 1-4. As best shown in FIG. 8, ring member 12 is C-shaped in cross section and has an outer peripheral opening 26 which is adapted to engage the tissue of the eye as described in my co-pending application, said description being herein incorporated by reference. The peripheral opening is defined by the lip edges 28 and 30 (FIG. 8). The resilient ring member 12 permits the lip edges 28 and 30 to grip the tissues of the eye as the eye tissue enters opening 26 and slightly spreads the lip edges 28 and 30 apart.

Figure 1:
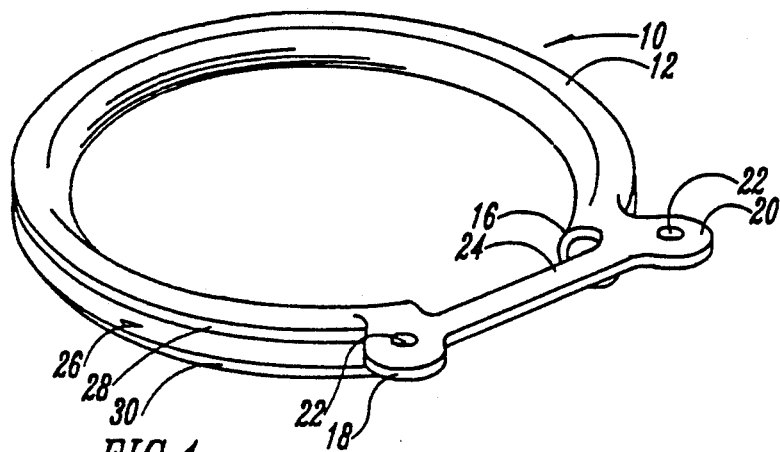
FIG. 1 is a perspective view of the pupil expander of my co-pending application.
Figure 2:
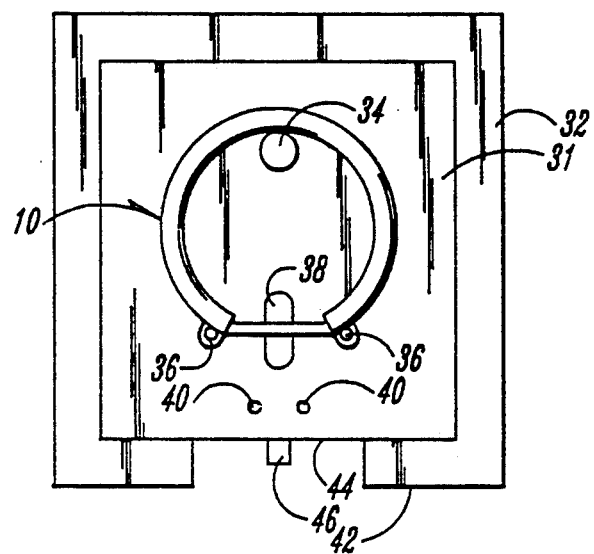
FIG. 2 is a plan view at a reduced scale of the carrier block of this invention with the pupil expander mounted thereon in its storage position.
Figure 3:
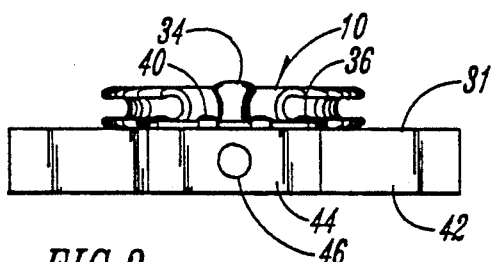
FIG. 3 is an end elevational view of the device of FIG. 2 as viewed from the bottom of FIG. 2.
Figure 4:
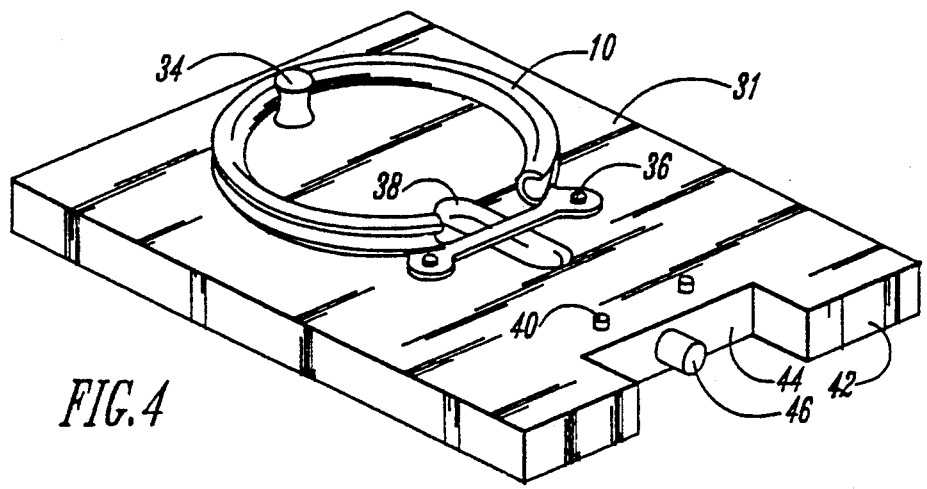
FIG. 4 is an enlarged scale perspective view of the device of FIG. 2.

With reference to FIGS. 2, 3 and 4, the carrier block 32 has an upper flat surface 31 with a first post 34. Post 34 has concave-shaped sides, and is spaced from a first pair of secondary posts 36 to form a triangular configuration. The posts 36 are of a diameter and spacing compatible with the apertures 22 in tabs 18 and 20 of pupil expander 10. In its storage position, the pupil expander assumes the position shown in FIGS. 2 and 4 wherein posts 36 penetrate apertures 22. In the storage position, the pupil expander shown in FIG. 1 is turned over so that the tabs 18 and 20 dwell directly on the flat surface 31. In this storage position, the apex of the pupil expander engages the post 34 as best shown in FIGS. 2 and 4.

An indented portion 38 exists in surface 31 underneath the strap 24 as best shown in FIGS. 2 and 4. The indented portion 38 facilitates the grasping of the strap 24 as will be discussed hereafter.

A second pair of secondary posts 40 extend vertically from surface 31 on the side of post 36 opposite to the post 34. As shown in FIGS. 2 and 4, the posts 40 are spaced apart but are closer together than are the posts 36. Posts 40 are also adapted to be received in the apertures 22 of pupil expander 10 as will be described hereafter.

A side edge 42 of carrier block 32 is adjacent the post 40. Edge 42 has notch 44 therein. A retention post 46 extends horizontally outwardly from the center of notch 44.

Figure 6:
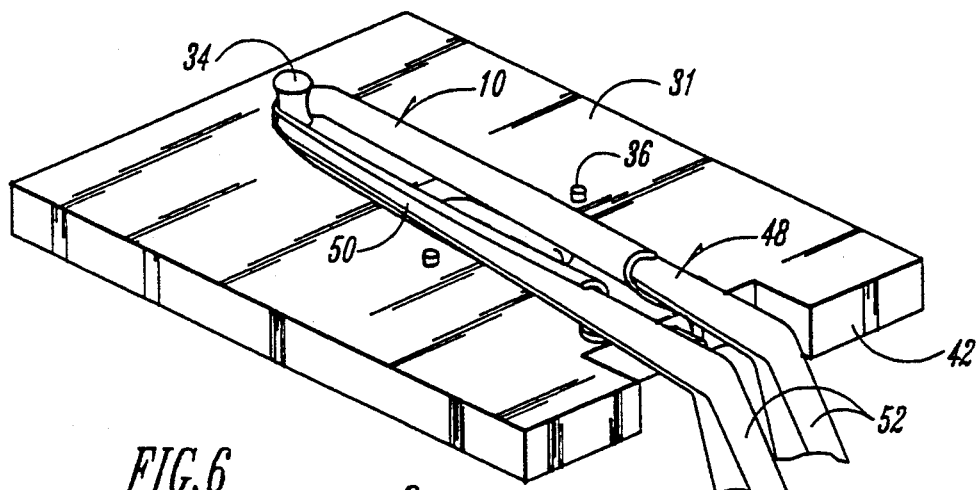
FIG. 6 is a perspective view similar to that of FIG. 5 but shows the forceps of this invention engaging the pupil expander for removal from the carrier block.
Figure 7:
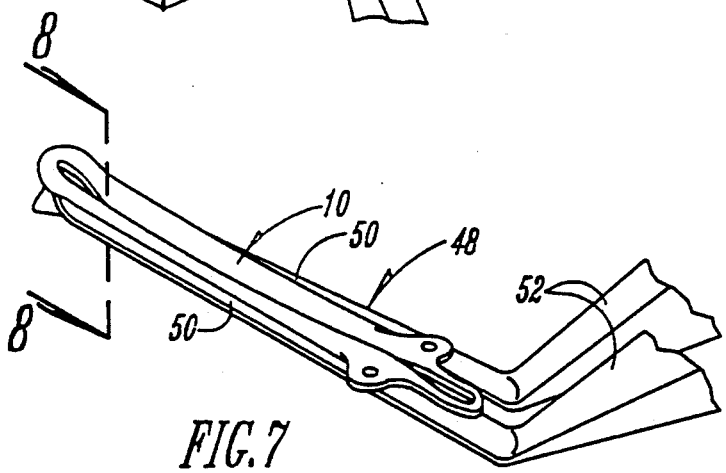
FIG. 7 is a partial perspective view of the forceps of this invention grasping the pupil expander after removal from the carrier block.

Forcep 48, except for the conventional handles thereon, is shown in FIG. 6 and 7. Forcep 48 is especially designed to accommodate the structure of the pupil expander 10. The forcep 48 has spaced forcep tips 50 which are elongated and which are rectangular in cross section. (FIG. 8) As seen in FIG. 8, the width of each forcep tip is greater than the height or thickness thereof. The width of each forcep tip 50 is approximately 0.70 mm, and the height or thereof is approximately 0.25 mm (0.0276" and 0.0098", respectively). The peripheral opening 26 of the hollow ring member 12 is approximately 0.2 mm (0.007"), and therefore easily receives from a lateral direction the forcep tips as shown in FIG. 8. It should be understood that the forcep tips can be yieldingly forced together in compressed condition as typical of forceps used in the medical field.

Figure 5:
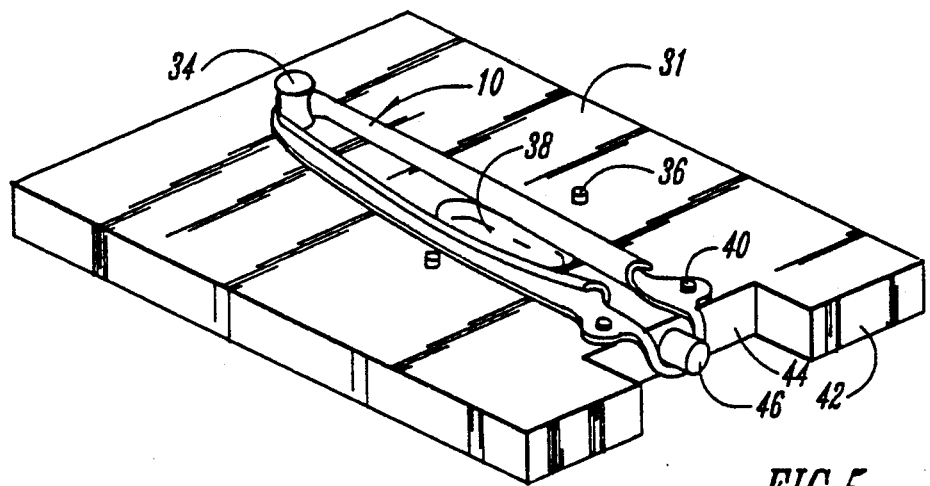
FIG. 5 is a perspective view similar to that of FIG. 4 but shows the pupil expander after it has been moved to its elongated position just prior to removal from the carrier.

In operation, when it is desired to insert the pupil expander 10 into the eye during a surgical procedure, as described in my co-pending application with said description being incorporated by reference herein, the forcep tips 50 are used to grasp the strap 24. Indented portion 38 facilitates this function. A vertical movement of the forcep tips lifts the tabs 18 and 20 from engagement with posts 36 whereupon the forcep is then pulled in a direction away from post 34 to elongate the ring member 12 to the position shown in FIG. 5. The apertures 22 are moved for insertion over the posts 40, and the strap 24 is pulled downwardly for retention around post 46 as best shown in FIG. 5. When stretched to the elongated condition of FIG. 5, the pupil expander is in a convenient position for removal and handling by the forcep tips 50. As shown in FIG. 6, the forcep tips 50 are moved longitudinally into the peripheral opening 26 of ring member 12. A further slight compression of the forcep tips permits the pupil expander to be lifted first upwardly over post 34 and then laterally detached from the retention post 46. In reality, this detachment of the pupil expander from the carrier block 32 takes place with essentially one continuous motion. The continued pressure of the forcep tips 50 on the pupil expander 10, as best in FIG. 7, retains the pupil expander in its elongated condition for insertion into the eye in accordance with the procedures outlined in my co-pending application.

When the forcep tips 50 have the rectangular cross section shown in FIG. 8, as compared to being circular or oval in cross section, the pupil expander 10 does not rotate on the forcep tips and is much easier to handle. This construction of the forcep tips has made it possible to insert the pupil expander into the eye with one hand because there is a great deal less friction between the rectangular forcep tip and the ring member 12.

The length of the forcep tips 50 is approximately 10.0 mm, and the tips 50 form an angle of approximately 45° with respect to the handles 52 of the forceps.

The carrier block of this invention and the special forceps used in conjunction with a pupil expander of my co-pending application o the carrier block greatly facilitate the delicate function of grasping the pupil expander, and inserting into the eye during a surgical procedure. It is, therefore, seen that this invention will accomplish all of its stated objectives.

What is claimed is:

1. In combination with a pupil expander having an elongated plastic resilient hollow circular ring member having a normal diameter and being arcuate in cross section and having an inner perimeter, and an outer perimeter with an outer peripheral opening to receive the inner perimeter of the iris of the human eye, said ring member having opposite spaced terminal end portions, a strap member integral with and secured to said terminal end portions and spanning the space therebetween, and holding said ring member in a substantially circular condition, and a pair of tabs adjacent said terminal end portions with apertures located in each of said tabs, a pupil expander carrier, comprising;

a block having a support surface,
   a first post extending upwardly from said support surface and engaging the inner periphery of said ring member,
   a first pair of spaced secondary posts extending upwardly from said support surface in spaced relation to said first post, with said first pair of secondary posts extending through the apertures in said tabs and adapted to engage and hold said ring member during storage conditions,
   a second pair of spaced secondary posts extending upwardly from said support surface and being spaced from said first post a distance greater than the normal diameter of said ring member whereby when said apertures in said tabs are moved from supporting engagement with said first pair of secondary posts to similar supporting engagement with said second pair of secondary posts, said ring member is changed from a circular configuration to an elongated and generally rectangular configuration.

2. The combination of claim 1 wherein said first post also is adapted to engage and hold said ring member in conjunction with either said first or second pair of secondary posts.

3. The combination of claim 1 wherein an indented portion is located in said support surface in a position generally underlaying said ring member to facilitate the grasping thereof by forceps.

4. The combination of claim 1 wherein said block has an edge portion adjacent said second pair of secondary posts, and a retention post extending outwardly therefrom to engage said strap member when said pupil expander is moved to its elongated and generally rectangular configuration.

5. The combination of claim 4 wherein said retention post is located within a notch in said edge portion.

6. The combination of claim 2 where said second pair of secondary posts are closer together than said first pair of secondary posts.

7. The combination of claim 1 where said second pair of secondary posts are closer together than said first pair of secondary posts.

* * * * *